United States Patent [19]

Hayakawa

[11] Patent Number: 4,535,161
[45] Date of Patent: Aug. 13, 1985

[54] BENZOQUINOLIZINE DERIVATIVES

[75] Inventor: Isao Hayakawa, Tokyo, Japan

[73] Assignee: Daiichi Seiyaku Co., Ltd., Tokyo, Japan

[21] Appl. No.: 507,635

[22] Filed: Jun. 27, 1983

[30] Foreign Application Priority Data

Dec. 10, 1982 [JP] Japan ................. 57-216545

[51] Int. Cl.³ .......................... C07D 401/10
[52] U.S. Cl. ........................ 546/94; 544/126; 544/361
[58] Field of Search ............ 546/94; 544/126, 361

[56] References Cited

U.S. PATENT DOCUMENTS 4,301,289 11/1981 Leir et al. ................. 546/94

Primary Examiner—Robert T. Bond
Attorney, Agent, or Firm—Sughrue, Mion, Zinn, Macpeak and Seas

[57] ABSTRACT

Benzoquinolizine derivatives of formula (I)

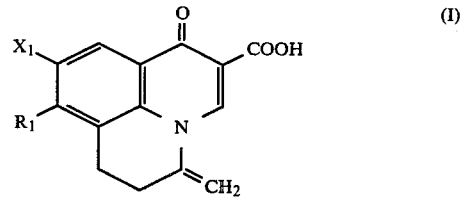

wherein:

$X_1$ represents a hydrogen atom or a halogen atom, $R_1$ represents a cyclic amino group which may contain additional hetero atom(s) of N,S and O and may be substituted with one or more substituents selected from the group consisting of hydroxyl, amino, alkyl, mono- or di-alkylamino, hydroxyalkyl and aminoalkyl, and physiologically acceptable salts thereof, having antibacterial activity.

5 Claims, No Drawings

BENZOQUINOLIZINE DERIVATIVES

FIELD OF THE INVENTION

This invention relates to novel benzoquinolizine derivatives which are useful as antibacterial agents.

BACKGROUND OF THE INVENTION

European Patent Application (OPI) No. 47005 describes 9-fluoro-10-substituted-3-methyl-7-oxo-2,3-dihydro-7H-pyrido-(1,2,3-de)-1,4-benzoxazine-6-carboxylic acid and West German Patent Application (OPI) No. 2914258 describes 9-fluoro-8-(4-methyl-1-piperazinyl)-5-methyl-6,7-dihydro--oxo-1H,5H-benz(ij)quinolizine-2-carboxylic acid (the term "OPI" as used herein refers to a "published unexamined application").

The present inventor found that introduction of a methylene group ($=CH_2$) into the tricyclic compounds brought the excellent antibacterial activity and completed this invention.

DETAILED DESCRIPTION OF THE INVENTION

This inventin relates to a novel antibacterial agent, and more particularly to benzoquinolizine derivatives of formula (I)

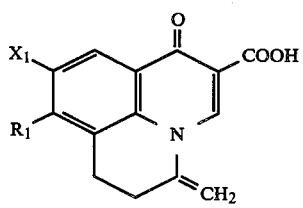

(I)

wherein:
$X_1$ represents a hydrogen atom or a halogen atom,
$R_1$ represents a cyclic amino group which may contain additional hetero atom(s) of N,S and O and may be substituted with one or more substituents selected from the group consisting of hydroxyl group, amino group, alkyl group, mono- or di-alkylamino group, hydroxyalkyl group and aminoalkyl group, and physiologically acceptable salts thereof.

In the description of this specification and claims, the alkyl groups have from 1 to 6 carbon atoms.

The cyclic amino group which may contain additional hetero atom(s) of N,S and O refers to groups derived from 4- to 7-membered heterocyclic compounds and examples of such groups include 1-azetidinyl, 1-pyrrolidinyl, 1-piperidinyl, 1-piperazinyl, 4-morpholinyl, 1-homopiperazinyl and the like as well as the substituted groups thereof such as 3-hydroxy-1-pyrrolidinyl, 3-alkylamino-1-pyrrolidinyl, 3-amino-1-pyrrolidinyl and 4-methyl-1-piperazinyl.

The compound of this invention can form an acid addition salt with an inorganic acid such as hydrochloric acid and sulfuric acid or an organic acid such as acidic amino acids, e.g. aspartic acid and glutamic acid, uronic acids, e.g. glucuronic acid and galacturonic acid, sulfonic acids, e.g. methanesulfonic acid, carboxylic acids, e.g. tartaric acid, and the like. Moreover, the compounds of this invention can form the corresponding carboxylate with an alkali metal or an alkaline earth metal such as sodium, potassium, calcium, and the like.

The compounds of this invention have excellent antibacterial activity against Gram-positive and Gram-negative bacteria, particularly, against *Pseudomonas aeruginosa*.

Referring to $X_1$ in the structural formula (I), halogen atom, especially, fluorine atom is preferred and referring to $R_1$, substituted pyrrolidinyl group, especially, 3-amino-1-pyrrolidinyl group and 3-hydroxy-1-pyrrolidinyl group are preferred. A particularly preferred class of compounds is those having formula (I) wherein $X_1$ is a fluorine atom and $R_1$ is a 3-hydroxy-1-pyrrolidinyl group or a 3-amino-1-pyrrolidinyl group and the most preferred embodiment is the compound of formula (I) wherein $X_1$ is a fluorine atom and $R_1$ is a 3-amino-1-pyrrolidinyl group.

The process for preparing the compound of formula (I) is illustrated by the following reaction scheme:

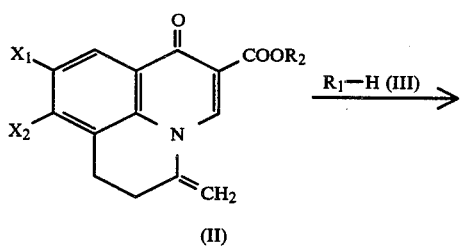

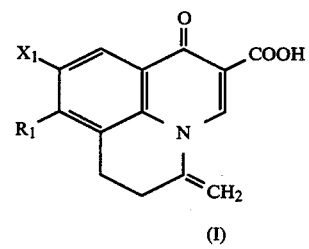

(I)

wherein
$X_1$ and $R_1$ are as defined above,
$X_2$ represents a halogen atom,
$R_2$ represents a hydrogen atom or an alkyl group.

The reaction of the compound of formula (II) with the compound of formula (III) is usually performed in the absence of solvent or in the presence of a polar solvent such as water, alcohols, dimethylformamide, dimethylacetamide, dimethyl sulfoxide, pyridine and the like for 1 hour to 6 hours at 50° C. to 200° C., preferably, at 100° C. to 150° C. Alternatively, the above reaction can be performed in the presence of an acid acceptor such as a tertiary amine, e.g. triethylamine and dimethylaniline, an inorganic base, e.g. potassium carbonate and the like, at a molar ratio of 1.0 to 1.2 of the acid acceptor per mole of the compound of formula (II). When the reaction is performed in the presence of acid acceptor, the compound of formula (III) can be preferably employed in 1.0 mole to 1.2 moles per mole of the compound of formula (II) and when the reaction is performed in the absence of the acid acceptor, the compound of formula (III) can be preferably employed in 2 moles to 5 moles per mole of the compound of formula (II).

When the compound of formula (III) is a cyclic amine substituted with an amino group, an aminoalkyl group or a mono-alkylamino group, the amino moiety is protected with a protecting group and the protected compound is allowed to react with the compound of formula (II). Thereafter, the protecting group can be eliminated from the resulting compound to produce the objective compound of formula (I).

The reactions used for eliminating the protecting group include a usual hydrolysis with an acid or a base and a usual catalytic reduction.

The hydrolysis is favorable for eliminating such protecting groups as tertiary butoxycarbonyl group, ethoxycarbonyl group, acyl group, e.g. acetyl group and trifluoroacetyl group, tosyl group and the like. And the catalytic reduction is favorable for eliminating such protecting groups as 4-methoxybenzyl group, benzyl group, benzhydryl group and the like.

When the compound of formula (II) wherein $R_2$ is an alkyl group is reacted with the compound of formula (III), the ester moiety of the product can be decomposed by hydrolysis with an acid or a base.

The hydrolysis of ester moiety with a base is usually performed in a solvent such as an aqueous alcohols or a mixture of water and an organic polar solvent, e.g. dimethyl sulfoxide and dimethylformamide, for 15 minutes to 2 hours at room temperature to 100° C. Examples of the base include an inorganic base such as an alkali metal or alkaline earth metal hydroxide or carbonate and the like. The base is usually employed in an amount of 1 mole to 5 moles per mole of the ester compound.

The hydrolysis of ester moiety with an acid is usually performed by heating the ester compound in an inorganic acid such as hydrochloric acid or a mixture of an inorganic acid and an alcohol such as methanol for 30 minutes to 5 hours under reflux or by heating the ester compound in a mixture of an inorganic acid and an organic acid such as acetic acid for 30 minutes to 5 hours at 100° C. to 130° C. The inorganic acid is usually employed in an amount of 2 moles to 10 moles per mole of the ester compound. When the inorganic acid is employed in excess, it can act as a solvent as well.

Apparently from the description with respect to the elimination of protecting group and decomposition of ester moiety, it is possible to complete the above two reacitons together by hydrolysis.

The starting material of formula (II) can be prepared by the process outlined below:

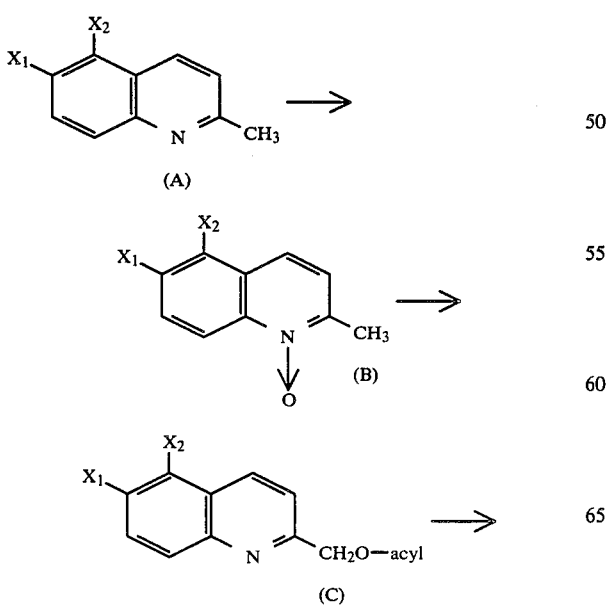

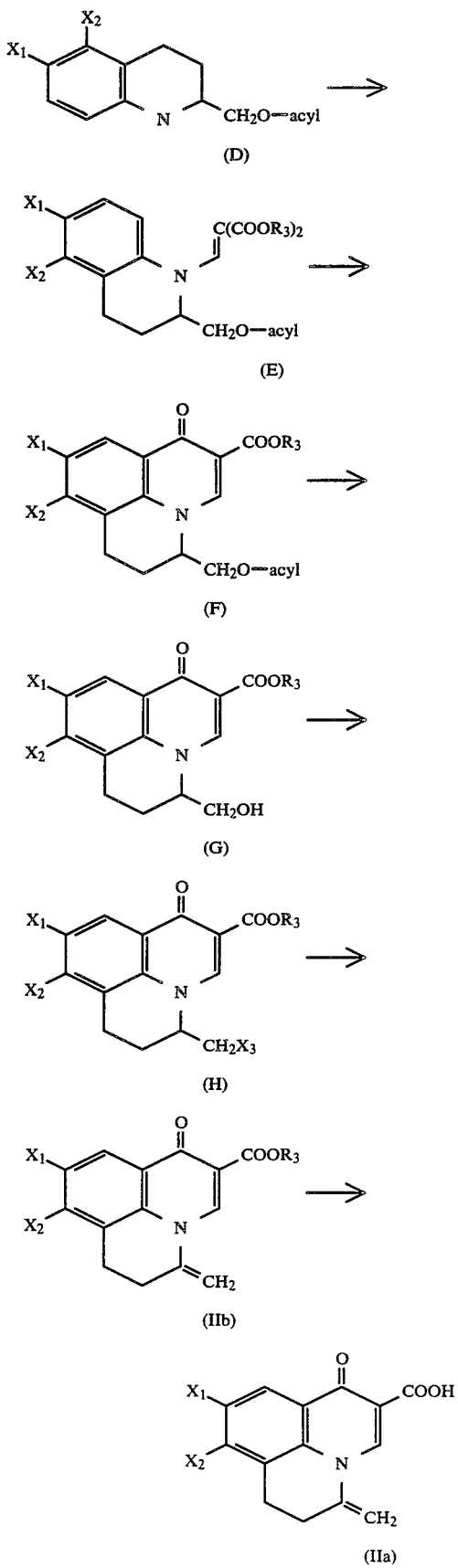

wherein $X_1$ and $X_2$ are as defined above, $X_3$ represents a halogen atom and $R_3$ represents an alkyl group.

That is, the compound of formula (A) is treated with a peroxydizing agent such as an organic peracid, e.g. 3-chloroperbenzoic acid, or hydrogen peroxide to produce the compound of formula (B) and the product is heated in an acid anhydride such as acetic anhydride to produce the compound of formula (C) and then the product is reduced in the presence of a catalyst such as platinum oxide, palladium black and the like under normal atmospheric pressure or under pressurized condition to produce the compound of formula (D). The compound of formula (D) is heated with a dialkyl alkoxymethylenemalonate to give the compound of formula (E) and the product is heated in a polyphosphoric acid or an ester thereof to produce the compound of formula (F) and then the product is selectively hydrolyzed to produce the compound of formula (G). The compound of formula (G) is treated with a halogenating agent such as thionyl chloride to produce the compound of formula (H) and the product is treated with an acid acceptor such as a tertiary amine, specifically, 1,8-diazabicyclo(5,4,0)7-undecene, to produce the compound of formula (IIb). The compound of formula (IIb) is hydrolyzed in a similar manner as that used for obtaining the objective compound from the ester compound to produce the compound of formula (IIa).

The antibacterial activity of the compounds of this invention is shown in the following Table 1.

TABLE 1

| Test Organism | MIC (mcg/ml)* | |
|---|---|---|
| | Ia | Ib |
| E. coli, NIHJ | 0.0125 | 0.0125 |
| Sh. flexneri, 2a, 5503 | 0.0125 | 0.0125 |
| Pr. vulgaris, 08602 | 0.05 | 0.025 |
| Pr. mirabilis, IFO-3849 | 0.10 | 0.025 |
| K. pneumoniae, type 1 | 0.10 | 0.05 |
| Ent. cloacae, 03400 | 0.05 | 0.0125 |
| Ser. marcescens, 10104 | 0.10 | 0.05 |
| Ps. aeruginosa, 32104 | 0.31 | 0.05 |
| Ps. aeruginosa, 32233 | 0.78 | 0.10 |
| Ps. aeruginosa, 32234 | 0.39 | 0.05 |
| Ps. aeruginosa, 32121 | 0.10 | 0.025 |
| Ps. aeruginosa, 32122 | 0.39 | 0.10 |
| S. aureus, 209 P | 0.05 | 0.10 |
| S. epidermidis, 56500 | 0.10 | 0.19 |
| Str. pyogenes, G-36 | 0.39 | 0.39 |
| Str. faecalis, ATCC-19433 | 0.39 | 0.39 |
| B. subtilis, ATCC-6633 | ≦0.0063 | 0.025 |

*Determined by the standard method of the Japan Society of Chemoterapy: (Mueller-Hinton Broth medium), $10^6$/ml of bacteria were seeded and incubated at 37° C. for 18 hours.
Ia: 9-fluoro-8-(3-hydroxy-1-pyrrolidinyl)-5-methylene-1-oxo-6,7-dihydro-1H,5H—benzo(ij)quinolizine-2-carboxylic acid
Ib: 8-(3-amino-1-pyrrolidinyl)-9-fluoro-5-methylene-1-oxo-6,7-dihydro-1H,5H—benzo(ij)quinolizine-2-carobxylic acid As can be seen in the Table 1, the compounds of this invention exhibit a very excellent antibacterial activity, particularly, 3-hydroxy-1-pyrrolidinyl compound (Ia) exhibits a very strong antibacterial activity against Gram-positive bacteria and 3-amino-1-pyrrolidinyl compound (Ib) exhibits a very strong antibacterial activity against Pseudomonas aeruginosa. The excellency is clearly comprehensible in comparing the Table 1 with the Tables in the specifications of EP Application (OPI) No. 47005 and DE Application (OPI) No. 2914258.

With respect to the toxicity of the compounds of this invention, the acute toxicity ($LD_{50}$) of the compound (Ib, hydrochloric acid addition salt) is 252 mg/kg as determined in mice (i.v.).

PRODUCTION OF STARTING MATERIAL 1.0 g of 5,6-difluoro-2-methylquinoline was dissolved in 30 ml of chloroform and then a mixture of 20 ml of chloroform and 1.0 g of 3-chloroperbenzoic acid was added dropwise thereto under cooling in an ice bath. The resulting mixture was stirred for 2 hours at 0° C. and for additional one hour at room temperature. The reaction mixture was washed twice with a saturated aqueous solution of sodium bicarbonate and washed with a saturated aqueous solution of sodium chloride. After drying, the solvent was distilled off in vacuo and the residue was purified by silica gel column chromatography to give 830 mg of 5,6-difluoro-2-methylquinoline-1-oxide. The product was recrystallized from a mixture of benzene and hexane to give a white powder with mp 125°–127° C.

Analysis for $C_{10}H_7F_2NO$: Calculated: C 61.54, H 3.62, N 7.18. Found: C 61.60, H 3.70, N 7.12.

550 mg of the above product was added to 20 ml of acetic anhydride and the mixture was allowed to react for 15 minutes at 140° C. The solvent was distilled off in vacuo and the residue was purified by silica gel column chromatography to give 430 mg of 2-acetoxymethyl-5,6-difluoroquinoline.

11.2 g of the above product was reduced in the presence of platinum oxide catalyst and methanol under high pressure (4.5 kg/cm$^2$) to give 4.45 g of 2-acetoxymethyl-5,6-difluoro-1,2,3,4-tetrahydroquinoline.

5.6 g of the above product was allowed to react with diethyl ethoxymethylenemalonate for 8 hours at 140° C. To 3.0 g of the product obtained 7.5 g of polyphosphate (prepared from phosphoric anhydride and ethanol) was added and the mixture was allowed to react for 40 minutes at 140° C. to give 610 mg of a product. The product was recrystallized from a mixture of ethanol and chloroform to give ethyl 5-acetoxy-methyl-8,9-difluoro-1-oxo-6,7-dihydro-1H,5H-benzo(ij)quinolizine-2-carboxylate with mp 201°–203° C. as colorless needles.

Analysis for $C_{18}H_{17}F_2NO_5$: Calculated: C 59.18, H 4.69, N 3.83. Found: C 58.93, H 4.73, N 3.91.

580 mg of the above product was suspended in 20 ml of ethanol and then 1 ml of a 2 normal aqueous solution of sodium hydroxide and 30 ml of chloroform were added thereto. The resulting mixture was stirred for 20 minutes at room temperature. The volume of the reaction mixture was reduced to a half volume by concentration in vacuo and 50 ml of water was added thereto. The precipitate formed was collected by filtration to give 360 mg of ethyl 8,9-difluoro-5-hydroxymethyl-1-oxo-6,7-dihydro-1H,5H-benzo(ij)quinolizine-2-carboxylate with mp 256°–258° C.

Analysis for $C_{16}H_{15}F_2NO_4 \cdot \frac{1}{4}H_2O$: Calculated: C 58.63, H 4.77, N 4.27. Found: C 58.59, H 4.57, N 4.38.

352 mg of the above product was suspended in 30 ml of chloroform and 3 ml of thionyl chloride was added thereto. The resulting mixture was refluxed for 30 minutes and the solvent was distilled off in vacuo. The residue was dissolved in chloroform and the mixture was washed with an aqueous solution of sodium bicarbonate and water and then dried over sodium sulfate. The solvent was distilled off and the residue was recrystallized from ethanol to give 342 mg of ethyl 5-chloromethyl-8,9-difluoro-1-oxo-6,7-dihydro-1H,5H-benzo(ij)quinolizine-2-carboxylate with mp 215°–218° C. as light yellow needles.

Analysis for $C_{16}H_{14}ClF_2NO_3$: Calculated: C 56.23, H 4.13, N 4.10. Found: C 56.06, H 4.14, N 4.04.

350 mg of the above product was suspended in 50 ml of dehydrated benzene and 350 mg of 1,8-diazabicyclo(5,4,0)-7-undecene (hereinafter abbreviated as DBU) was added thereto. The resulting mixture was refluxed for 2 hours. 300 mg of DBU was added to the reaction mixture and the resulting mixture was refluxed for 3 days. The solvent was distilled off in vacuo. The residue was purified by silica gel column chromatography and then recrystallized from ethanol to give 253 mg of ethyl 8,9-difluoro-5-methylene-1-oxo-6,7-dihydro-1H,5H-benzo(ij)quinolizine-2-carboxylate with mp 272°–274° C. as colorless needles.

Analysis for $C_{16}H_{13}F_2NO_3$: Calculated: C 62.95, H 4.29, N 4.59. Found: C 62.91, H 4.30, N 4.59.

240 mg of the above product was added to a mixture of 1 ml of a 1 normal aqueous solution of sodium hydroxide, 20 ml of water and 30 ml of ethanol and then the resulting mixture was allowed to react for 30 minutes at 40°–50° C. Ethanol was distilled off and 40 ml of a 10% aqueous solution of citric acid was added thereto. The precipitate formed was collected by filtration and recrystallized from ethanol to give 180 mg of 8,9-difluoro-5-methylene-1-oxo-6,7-dihydro-1H,5H-benzo(ij)quinolizine-2-carboxylic acid with mp 220°–232° C.

NMR (DMSO-$d_6$, δ ppm): 5.30, 5.61 (each 1H, J=3.0 Hz, $C_5=CH_2$).

Analysis for $C_{14}H_9F_2NO_3$: Calculated: C 60.66, H 3.27, N 5.05. Found: C 60.69, H 3.52, N 5.02.

EXAMPLE 1

150 mg of 8,9-difluoro-5-methylene-1-oxo-6,7-dihydro-1H,5H-benzo(ij)quinolizine-2-carboxylic acid was suspended in 3 ml of dimethyl sulfoxide and 150 mg of 3-tertiary-butoxycarbonylaminopyrrolidine was added thereto. The resulting mixture was allowed to react for 3.5 hours at 120° C. The solvent was distilled off and the residue was purified by preparative thin layer chromatography on silica gel to give a crude product.

6 ml of trifluoroacetic acid and 250 mg of anisole were added to the above product and the resulting mixture was stirred for one hour at room temperature. The solvent was distilled off and then 4 ml of a saturated aqueous solution of sodium bicarbonate and 10 ml of methanol were added to the residue to dissolve it. The solvent was distilled off. The residue was purified by column chromatography on HP 20 (Diaion HP-20, a product of Mitsubishi Chemical Industries Ltd.) and purified by high performance liquid chromatography on μBondapac $C_{18}$ (a product of Waters Associates) using a mixture of water and acetonitrile (2:1 by volume) for elution and then recrystallized from ethanol to give 43 mg of 8-(3-amino-1-pyrrolidinyl)-9-fluoro-5-methylene-1-oxo-6,7-dihydro-1H,5H-benzo(ij)quinolizine-2-carboxylic acid as microcrystals with decomposing point 152°–170° C.

NMR (DMSO-$d_6$, δ ppm): 1.70, 2.10 (each 1H, m, $C_4$—H of pyrrolidine); 2.77, 3.02 (each 2H, t, $C_6$— and $C_7$—H); 3.2–3.6 (5H, m, pyrrolidine); 5.26, 5.58 (each 1H, d, J≦2 Hz, $C_5=CH_2$); 7.84 (1H, d, J=14 Hz, $C_{10}$—H); 8.80 (1H, s, $C_3$—H).

Analysis for $C_{18}H_{18}FN_3O_3 \cdot \frac{3}{4}H_2O$: Calculated: C 60.58, H 5.51, N, 11.77. Found: C 60.57, H 5.61, N 11.51.

EXAMPLE 2

4 ml of dimethyl sulfoxide and 100 mg of 3-hydroxypyrrolidine were added to 100 mg of 8,9-difluoro-5-methylene-1-oxo-6,7-dihydro-1H,5H-benzo(ij)quinolizine-2-carboxylic acid and the resulting mixture was allowed to react for 2 hours at 120° C. The solvent was distilled off. The residue was purified by silica gel column chromatography and purified by preparative thin layer chromatography on silica gel and then recrystallized from a mixture of ethanol and chloroform to give 28 mg of 9-fluoro-8-(3-hydroxy-1-pyrrolidinyl)-5-methylene-1-oxo-6,7-dihydro-1H,5H-benzo(ij)quinolizine-2-carboxylic acid as microcrystals with mp 190°–196° C.

NMR (CDCl$_3$, δ ppm): 5.16, 5.41 (each 1H, d, J=2 Hz, $C_5=CH_2$); 8.04 (1H, d, J=14 Hz, $C_{10}$—H); 8.97 (1H, s, $C_3$—H).

Analysis for $C_{18}H_{17}FN_2O_4 \cdot \frac{1}{4}H_2O$: Calculated: C 61.97, H 5.06, N 8.02. Found: C 62.24, H 4.80, N 8.19.

EXAMPLE 3

400 mg of N-methylpiperazine and 6 ml of dimethyl sulfoxide were added to 400 mg of 8,9-difluoro-5-methylene-6,7-dihydro-1-oxo-1H,5H-benzo(ij)quinolizine-2-carboxylic acid and the resulting mixture was heated for 2.5 hours at 100°–110° C. (bath temperature). The solvent was distilled off in vacuo and water was added to the residue. The mixture was extracted with chloroform and the extract was dried. The solvent was distilled off and the residue was purified by silica gel column chromatography and then recrystallized from ethanol to give 85 mg of 8-(4-methyl-1-piperazinyl)-9-fluoro-5-methylene-6,7-dihydro-1-oxo-1H,5H-benzo(ij)quinolizine-2-carboxylic acid as microcrystals with 282°–285° C. (decomposition).

Analysis for $C_{19}H_{20}N_3O_3F \cdot \frac{1}{4}H_2O$: Calculated: C 63.06, H 5.71, N 11.61. Found: C 63.16, H 5.64, N 11.50.

EXAMPLE 4

1.5 ml of 2 normal hydrochloric acid and 20 ml of methanol were added to 600 mg of 8-(3-amino-pyrrolidinyl)-9-fluoro-5-methylene-6,7-dihydro-1-oxo-1H,5H-benzo(ij)quinolizine-2-carboxylic acid to dissolve it. The solvent was distilled off at a temperature slightly lower than room temperature. Ethanol was added to the residue and the mixture was concentrated to dryness in vacuo and methanol was added to the residue. The precipitate formed was collected by filtration and washed with ethanol and diethyl ether and then dried. The precipitate was recrystallized from methanol to give 245 mg of the corresponding hydrochloric acid salt. The salt melted at 182°–187° C. with gradual decomposition.

Analysis for $C_{18}H_{18}FN_3O_3 \cdot HCl \cdot H_2O$: Calculated: C 54.34, H 5.32, N 10.56. Found: C 54.09, H 5.32, N 10.36.

What is claimed is:

1. A benzoquinolizine derivative of formula (I)

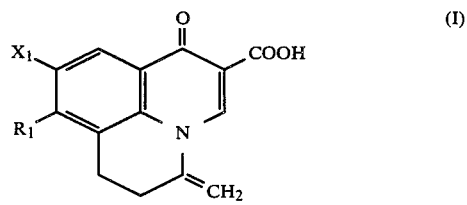

wherein:

$X_1$ represents a hydrogen atom or a halogen atom and $R_1$ represents a 4- to 7-membered saturated cyclic amino group selected from the group consisting of a 1-azetidinyl, a substituted pyrrolidinyl, 1-piperidinyl, 1-piperazinyl and 4-morpholinyl which may be substituted with one or more substituents selected from the group consisting of hydroxyl group, amino group, alkyl group, mono- or di-alkylamino group, hydroxyalkyl group and aminoalkyl group, wherein the alkyl moiety in said one or more substituents contains 1 to 6 carbon atoms, a nitrogen atom of said cyclic amino group being bonded to the benzoquinolizine moiety, and physiologically acceptable salts thereof.

2. A compound as claimed in claim 1, wherein $X_1$ is a fluorine atom.

3. A compound as claimed in claim 1, wherein $X_1$ is a fluorine atom and $R_1$ is a substituted pyrrolidinyl group.

4. A compound as claimed in claim 1, wherein $X_1$ is a fluorine atom and $R_1$ is a 3-hydroxy-1-pyrrolidinyl group.

5. A compound as claimed in claim 1, wherein $X_1$ is a fluorine atom and $R_1$ is a 3-amino-1-pyrrolidinyl group.

* * * * *